United States Patent
Masahiro et al.

(10) Patent No.: US 10,125,158 B2
(45) Date of Patent: Nov. 13, 2018

(54) METHOD FOR MANUFACTURING IRIDIUM COMPLEX

(71) Applicant: TANAKA KIKINZOKU KOGYO K.K., Chiyoda-ku, Tokyo (JP)

(72) Inventors: Yasushi Masahiro, Tokyo (JP); Toshiyuki Shigetomi, Tsukuba (JP); Junichi Taniuchi, Tsukuba (JP); Ryosuke Harada, Tsukuba (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 15/503,822

(22) PCT Filed: Aug. 28, 2015

(86) PCT No.: PCT/JP2015/074374
§ 371 (c)(1),
(2) Date: Feb. 14, 2017

(87) PCT Pub. No.: WO2016/043016
PCT Pub. Date: Mar. 24, 2016

(65) Prior Publication Data
US 2017/0253623 A1  Sep. 7, 2017

(30) Foreign Application Priority Data
Sep. 19, 2014  (JP) .................................. 2014-191385

(51) Int. Cl.
| C07C 45/77 | (2006.01) |
| C07F 15/00 | (2006.01) |
| C07C 49/92 | (2006.01) |
| C09K 11/06 | (2006.01) |
| C23C 16/18 | (2006.01) |
| H01L 51/00 | (2006.01) |
| H01L 51/50 | (2006.01) |

(52) U.S. Cl.
CPC ............ *C07F 15/004* (2013.01); *C07C 45/77* (2013.01); *C07C 49/92* (2013.01); *C09K 11/06* (2013.01); *C23C 16/18* (2013.01); *H01L 51/0085* (2013.01); *C07F 15/00* (2013.01); *C09K 2211/185* (2013.01); *H01L 51/0002* (2013.01); *H01L 51/5016* (2013.01)

(58) Field of Classification Search
CPC .......... C07C 45/77; C07C 49/92; C07F 15/00
USPC ........................................................ 556/40
See application file for complete search history.

(56) References Cited

U.S. PATENT DOCUMENTS 6,663,706 B2 * 12/2003 Saito ...................... C23C 16/18
106/287.18

FOREIGN PATENT DOCUMENTS

| JP | 7-316176 A | 12/1995 |
| JP | 2003-64019 A | 3/2003 |
| JP | 2003-321415 A | 11/2003 |
| JP | 2003-321416 A | 11/2003 |
| JP | 2003321415 A * | 11/2003 |
| JP | 2003321415 A * | 11/2003 |
| JP | 2005-531590 A | 10/2005 |
| JP | 2012-006914 A | 1/2012 |

OTHER PUBLICATIONS

JP 2003321415 A—Machine Translation.*
Machine Translation of Toyama (JP2003321415A). (Year: 2003).*
PCT, International Search Report for PCT/JP2015/074374, dated Nov. 10, 2015.
Zhang et al., A New Synthetic Route to the Preparation of a Series of String Photoreducing Agents: fac Tris-Ortho-Metalated Complexes of Iridium (III) with Substituted 2-Phenylpyridines, Inorg. Chem. 1991, vol. 30, pp. 1685-1687, American Chemical Society.
EP, Extended Search Report for European application No. 15842524.9, dated Apr. 4, 2018.
Davignon et al. "Etude cristallographique du tris (pentanedione-2,4) iridium(III), du tris (trifluoro-1,1-1 pentanedione-2,4) rhodium(III) et du tris (trifluoro-1,1-1 pentanedione-2,4) iridium (III)." Journal of the Less-Common Metals, Elsevier-Sequoia S.A. Lausanne, CH, vol. 21, No. 3, Jul. 1, 1970, pp. 345-351, XP024075652, ISSN: 022-5088.

* cited by examiner

*Primary Examiner* — Clinton A Brooks
*Assistant Examiner* — Kofi Adzamli
(74) *Attorney, Agent, or Firm* — Orrick, Herrington & Sutcliffe LLP; Joseph A. Calvaruso

(57) ABSTRACT

A method for manufacturing tris(β-diketonato)iridium by reacting β-diketone with an iridium compound, in which an activation treatment including (a) an alkali treatment and (b) an acid treatment described below is applied to the iridium compound to activate the iridium compound, and to subsequently react the β-diketone, (a) an alkali treatment: a treatment of adding alkali to a solution of the iridium compound to raise pH of the solution to a more alkaline side than that before the alkali addition and to not less than 10, and (b) an acid treatment: a treatment of adding acid to the solution subjected to the alkali treatment to lower pH of the solution to a more acidic side than that before the acid addition and to make the pH difference between solutions before and after the acid addition be not less than 0.1 and not more than 10. The present invention allows manufacture of tris(β-diketonato)iridium utilizing a wide variety of β-diketones.

7 Claims, No Drawings

METHOD FOR MANUFACTURING IRIDIUM COMPLEX

TECHNICAL FIELD

The present invention relates to a method for manufacturing tris(β-diketonato)iridium being an iridium complex in which β-diketone is coordinated to iridium. In particular, it relates to a method that can synthesize iridium complexes by coordinating a wide variety of β-diketones to iridium.

BACKGROUND ART

Tris(β-diketonato)iridium composed of iridium coordinated with β-diketone is known as a raw material compound (precursor) for use in chemical deposition methods such as a CVD method (chemical vapor deposition method) and an ALD method (atomic layer deposition method). For example, in Patent Literatures 1 and 2, there is described a raw material compound for chemical deposition for forming an iridium thin film composed of tris(5-methyl-2,4-hexanedionato)iridium or tris(2,4-octanedionato)iridium as an iridium complex.

Further, in recent years, there is investigated the application of a cyclometalated iridium complex, in which a multidentate ligand is coordinated annularly to iridium, to phosphorescent materials for an organic light-emitting element such as an organic electroluminescence (EL) element or an organic electrochemiluminescence (ECL) element (Patent Literature 3). Furthermore, tris(β-diketonato)iridium is also useful as a raw material (intermediate material) for manufacturing a phosphorescent material for an organic light-emitting element such as the cyclometalated iridium complex. For example, in Non Patent Literature 1, there is disclosed a method for manufacturing a phosphorescent material for an organic light-emitting element composed of cyclometalated iridium, by using tris(2,4-pentanedionato)iridium as a raw material and reacting the raw material with an aromatic heterocyclic bidentate ligand such as 2-phenylpyridine (ppy).

Here, as a method for manufacturing tris(β-diketonato)iridium, a process is known which uses an iridium salt such as iridium trichloride as a starting material, adds a β-diketone to be a ligand to the material, and adds potassium bicarbonate or the like to make the material alkaline and to react these (PTL 4).

The conventional synthesis method may synthesize directly above-described tris(5-methyl-2,4-hexanedionato)iridium, tris(2,4-octanedionato)iridium and tris(2,4-pentanedionato)iridium. However, the investigation by the present inventors confirms that the progress of a reaction is difficult in the conventional synthesis method in manufacturing of iridium complexes in which a wide range of β-diketones are coordinated.

For example, as for the above-described cyclometalated iridium complex as a phosphorescent material, it is necessary to investigate complexes coordinated with various ligands aiming at improvement in a luminous efficiency. In order to obtain a starting material for such a cyclometalated iridium complex, the inventors of the present application tried to synthesize iridium complexes in which a β-diketone was coordinated, the β-diketone having various structures containing an element such as fluorine excluding hydrogen/carbon, cyclic hydrocarbon, or the like, but did not recognize the progress of a synthesis reaction with the conventional method, and failed to obtain targeted tris(β-diketonato)iridium.

CITATION LIST

Patent Literature

PTL 1: Japanese Patent No. 4054215
PTL 2: Japanese Patent No. 4856825
PTL 3: Japanese Patent Laid-Open Publication No. 2012-6914
PTL 4: Japanese Patent Laid-Open Publication No. 07-316176

Non Patent Literature

NPL 1: Inorg. Chem., vol. 30, p 1685, 1991

SUMMARY OF INVENTION

Technical Problem

Consequently, the present invention provides a method for manufacturing tris(β-diketonato)iridium, the method capable of progressing a synthesis reaction to without a restriction of the range of β-diketone to be coordinated.

Solution to Problem

The main point of problem in the present invention is that an iridium compound loses almost completely reactivity relative to β-diketones lying outside a certain range with a general synthesis method. The earnest examination of the problem by the present inventors revealed that a prescribed activation treatment was applied to an iridium compound to be a starting material to activate the iridium compound, thereby developing reactivity also to the above-described β-diketones and making it possible to synthesize targeted tris(β-diketonato)iridium.

That is, the present invention is a method for manufacturing tris(β-diketonato)iridium shown by Chem. 2 in which a β-diketone is coordinated to iridium, by reacting the β-diketone shown by Chem. 1 with an iridium compound, wherein an activation treatment including (a) an alkali treatment and (b) an acid treatment described below is applied to the iridium compound to activate the iridium compound, and to subsequently react the β-diketone.

(a) An alkali treatment: a treatment of adding alkali to a solution of the iridium compound to raise pH of the solution to a more alkaline side than that before the addition and to not less than 10.

(b) An acid treatment: a treatment of adding acid to the solution subjected to the alkali treatment to lower pH of the solution to a more acidic side than that before the acid addition and to make the pH difference between solutions before and after the acid addition be not less than 0.1 and not more than 10.

[Chem. 1]

wherein each of $R^a$ and $R^b$ is a hydrocarbon group or substituents in which a hydrogen atom in a hydrocarbon group is substituted by a halogen atom. $R^a$ and $R^b$ may be different substituents, or the identical substituent. $R^c$ is a substituent composed of any of a hydrogen atom, a halogen atom and a hydrocarbon group.

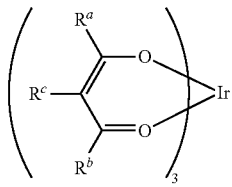

[Chem. 2]

wherein $R^a$, $R^b$, and $R^c$ have the same meaning as in Chem. 1.

Hereinafter, there will be described in detail the contents of respective steps in the present inventive method for manufacturing an iridium complex (tris(β-diketonato) iridium).

A wide range of iridium compounds are applicable to an iridium compound for use as a starting material in the present invention. For example, nitrate, sulfate, hydroxide, halide etc. of iridium can be applied. More concretely, it is possible to apply iridium nitrate, iridium sulfate, iridium hydroxide, ammonium hexachloroiridate, iridium chloride, chloroiridic acid, potassium chloroiridate, sodium chloroiridate, iridium bromide, bromoiridic acid, potassium bromoiridate, sodium bromoiridate, iridium iodide, iridium oxide etc. The valence number of iridium in these iridium compounds may be three or four.

However, when the final yield of tris(β-diketonato) iridium is considered, suitable iridium compounds are iridium nitrate (III, IV), iridium chloride (III, IV), and ammonium hexachloroiridate (III, IV). These iridium compounds have a comparatively weak bond between iridium and an anion. For the progress of a synthesis reaction of tris(β-diketonato)iridium, each of the progress of decomposition of an iridium compound being a starting material and the progress to conjugate base deprotonated from β-diketone is necessary, and therefore the application of the preferable iridium compounds enables an effective complex synthesis.

An iridium compound is offered to a reaction in a state of a solution. Water is preferable as a solvent for an iridium compound solution. The concentration of an iridium compound in the solution is preferably not less than 0.01 mol/L and not more than 20 mol/L. Meanwhile, pH of the solution of an iridium compound is frequently in a range of not less than 0 and not more than 12.

Further, the present invention applies an activation treatment including the alkali treatment and the acid treatment to the solution of an iridium compound. These treatments have an action of activating the iridium compound and progressing the synthesis reaction of tris(β-diketonato)iridium.

The alkali treatment is a treatment of adding alkali to a solution of the iridium compound to raise pH thereof to a more alkaline side than that before the alkali addition and to not less than 10. The alkali treatment more preferably raises the pH of a solution of the iridium compound to not less than 12. Alkali to be added at this time is preferably sodium hydroxide, potassium hydroxide, lithium hydroxide, cesium hydroxide, barium hydroxide, sodium carbonate, potassium carbonate, sodium bicarbonate, potassium bicarbonate, ammonia or tetramethylammonium hydroxide. Alkali is preferably added in a state of a solution, and concentration of the alkaline solution is preferably not less than 0.01 mol/L and not more than 20 mol/L. The solution of an iridium compound subjected to the alkali treatment, preferably, is left at rest for not less than 0.5 hours and not more than 24 hours in the pH range and then subjected to a subsequent treatment (acid treatment). Further, the alkali treatment shifts pH of the solution of an iridium compound to an alkaline side, and the pH difference between solutions before and after the alkali addition in the treatment is set preferably to not less than 2 and not more than 13, and more preferably to not less than 5 and not more than 13.

The acid treatment to be applied subsequent to the alkali treatment is a treatment of adding acid to the solution of an iridium compound in an alkaline region to make the pH difference between before and after the acid addition be not less than 0.1 and not more than 10 while lowering pH to a more acidic side than that before the acid addition. Acid to be added here is preferably nitric acid, hydrochloric acid, hydrobromic acid, hydroiodic acid, hypochlorous acid, chlorous acid, chloric acid, perchloric acid, phosphoric acid, sulfuric acid, hexafluoroantimonic acid, tetrafluoroboric acid, hexafluorophosphoric acid, chromic acid, boric acid, methanesulfonic acid, ethanesulfonic acid, benzenesulfonic acid, p-toluenesulfonic acid, trifluoromethanesulfonic acid, acetic acid, citric acid, formic acid, gluconic acid, lactic acid, oxalic acid or tartaric acid. Acid concentration of an acid solution to be added is preferably not less than 0.01 mol/L and not more than 20 mol/L. Meanwhile, pH difference between before and after the acid addition in the acid treatment is preferably not less than 1 and not more than 10.

The iridium compound is activated by the activation treatment including the alkali treatment and the acid treatment as described above. The activation of the iridium compound is exerted at the stage when each of the alkali treatment and the acid treatment has been applied. In addition, the alkali treatment precedes the acid treatment in the order. Further, each of the alkali treatment and the acid treatment can be applied at room temperature. Concretely, the activation treatment can be applied at not less than 0° C. and not more than 50° C.

The complex synthesis progresses by the reaction of the iridium compound after the activation treatment with a β-diketone. The β-diketone to be reacted here is a β-diketone to be coordinated to iridium in an iridium complex to be manufactured, that is, the β-diketone shown by the formula of Chem. 1.

Each of $R^a$ and $R^b$ in the β-diketone of the formula of Chem. 1 is a hydrocarbon group or substituents in which a hydrogen atom in a hydrocarbon group is substituted by a halogen atom. When $R^a$ and/or $R^b$ is a hydrocarbon group, the hydrocarbon group is preferably an aliphatic hydrocarbon group or an aromatic hydrocarbon group. Moreover, groups in which a hydrogen atom in the hydrocarbon groups is substituted by a halogen atom are also preferable.

More concretely, when $R^a$ and/or $R^b$ is an aliphatic hydrocarbon group, the hydrocarbon group is preferably in a linear chain shape or in a branched chain shape. Further, an aliphatic hydrocarbon group having carbon number of 1 to 10 is preferable. For example, an alkyl group (more preferably carbon number 1 to 5), a cycloalkyl group and a neopentyl group are mentioned. More concretely, to name several examples, they are a methyl group, an ethyl group, a propyl group, an isopropyl group, a n-butyl group, a t-butyl group, a n-octyl group, a n-decyl group, a n-hexadecyl group, a cyclopropyl group, a cyclopentyl group, a cyclohexyl group, a neopentyl group. Further, groups in which a hydrogen atom in the aliphatic hydrocarbon groups is substituted by fluorine are also preferable. Meanwhile, $R^a$ and $R^b$ may be different substituents or the identical substituent.

When $R^a$ and/or $R^b$ is an aromatic hydrocarbon group, an aromatic hydrocarbon group that has carbon number of 6 to 20 is preferable. More preferable is an aromatic hydrocarbon group that has a carbon number of 6 to 10. Concretely, there are a phenyl group, a naphthyl group, a biphenyl group, a fluorenyl group, a phenanthryl group, an anthracenyl group, a triphenylenyl group, a terphenyl group, a pyrenyl group, a mesityl group, a tolyl group, a xylyl group, an azulenyl group, an acenaphthenyl group, an indenyl group etc. Further, groups, in which a hydrogen atom in the aromatic hydrocarbon groups is substituted by fluorine, are also preferable. Meanwhile, $R^a$ and $R^b$ may be different substituents or the identical substituent.

In addition, $R^c$ is a substituent composed of any of a hydrogen atom, a halogen atom and a hydrocarbon group. When the substituent $R^c$ is a halogen atom, the substituent is most preferably a fluorine atom. When $R^c$ is a hydrocarbon group, the hydrocarbon group is preferably in a linear chain shape or in a branched chain shape. Further, an aliphatic hydrocarbon group having carbon number of 1 to 10 is preferable. For example, there are mentioned an alkyl group (more preferably carbon number is 1 to 5), a cycloalkyl group and a neopentyl group. More concretely, to name several examples, they are a methyl group, an ethyl group, a propyl group, an isopropyl group, a n-butyl group, a t-butyl group, a n-octyl group, a n-decyl group, a n-hexadecyl group, a cyclopropyl group, a cyclopentyl group, a cyclohexyl group, a neopentyl group. Further, groups, in which a hydrogen atom in the aliphatic hydrocarbon groups is substituted by fluorine, are also preferable.

As concrete examples of β-diketones in consideration of the above description, β-diketones below can be reacted.

[Chem. 3]

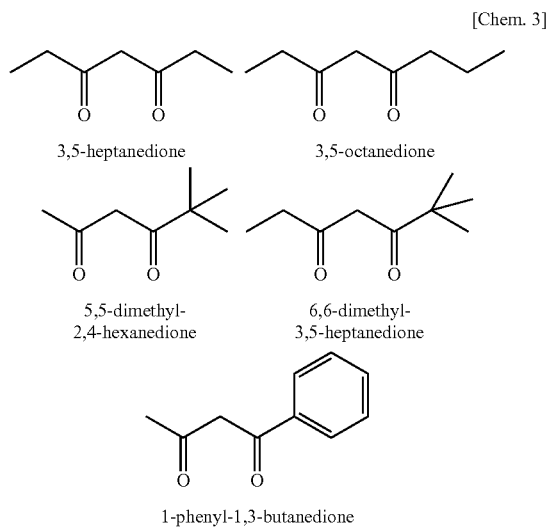

[Chem. 4]

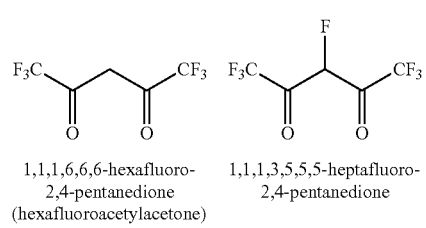

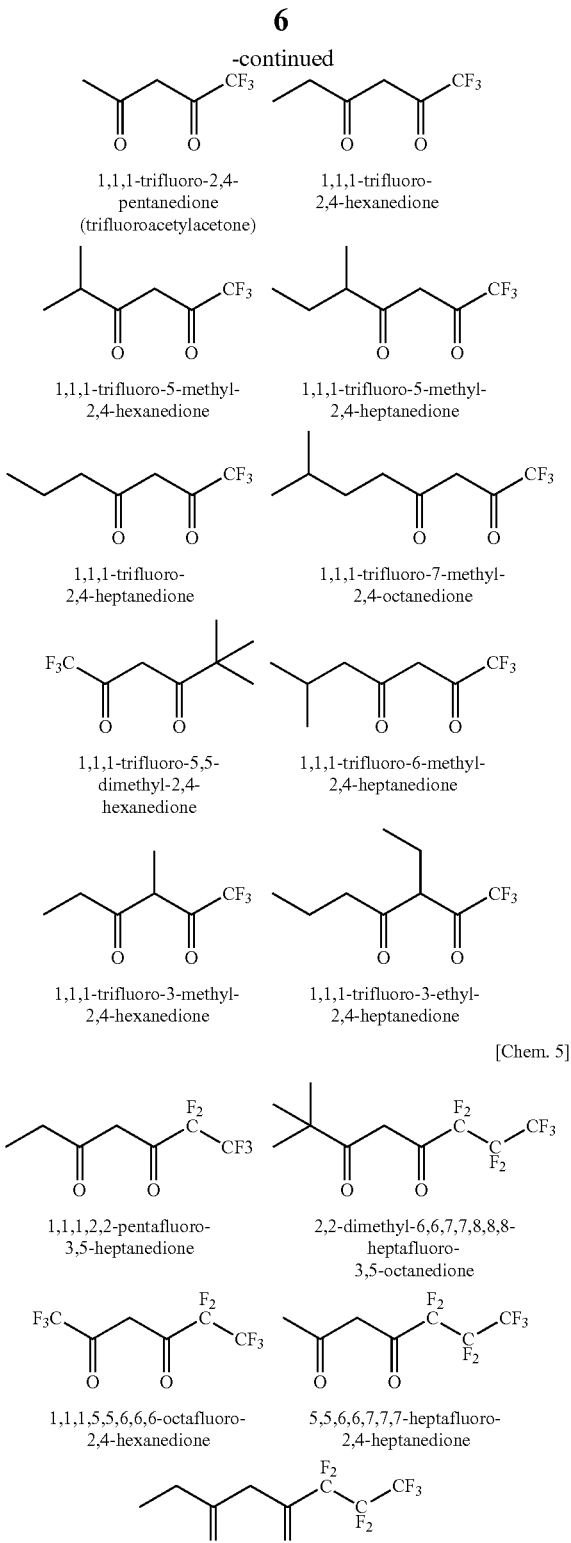

[Chem. 5]

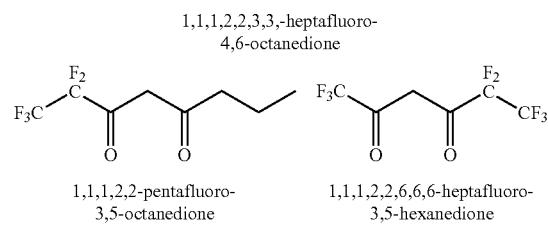

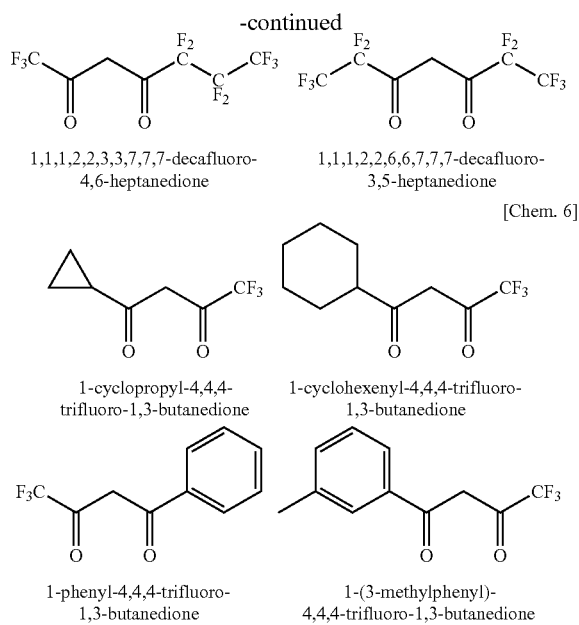

1,1,1,2,2,3,3,7,7,7-decafluoro-4,6-heptanedione 1,1,1,2,2,6,6,7,7,7-decafluoro-3,5-heptanedione

[Chem. 6]

1-cyclopropyl-4,4,4-trifluoro-1,3-butanedione 1-cyclohexenyl-4,4,4-trifluoro-1,3-butanedione 1-phenyl-4,4,4-trifluoro-1,3-butanedione 1-(3-methylphenyl)-4,4,4-trifluoro-1,3-butanedione Incidentally, a concrete operation for reacting an activated iridium compound with a β-diketone is to add the β-diketone to an iridium compound solution. As to timing of adding the β-diketone to the iridium compound solution, the β-diketone may be added to the iridium compound solution after the completion of the activation treatment, or the β-diketone may be added to the iridium compound solution before the completion of the activation treatment and then the activation treatment may be applied.

When a β-diketone is added to an iridium compound solution after the completion of the activation treatment, the solution after the activation treatment can be offered directly to a synthesis reaction. However, depending on the type of a raw material compound, precipitates may be generated by the activation treatment. In this case, it may also be possible to collect precipitates by filtration and disperse the precipitates in water, and to add the β-diketone to the dispersion liquid. Further, the synthesis reaction of tris(β-diketonato)iridium progresses by addition of the β-diketone to a solution after the activation treatment or to a dispersing solution of precipitates.

On the other hand, a technical meaning of the addition of a β-diketone to an iridium compound solution before the completion of the activation treatment includes each of a case in which the β-diketone is added previously to the iridium compound solution before the application of each of the alkali treatment and the acid treatment, and a case of the addition in a halfway stage of the activation treatment, that is, a case in which the β-diketone is added to the iridium compound solution between the alkali treatment and the acid treatment.

When a β-diketone is added to an iridium compound solution before the completion of the activation treatment, the synthesis reaction of tris(β-diketonato)iridium does not progress at the addition stage of the β-diketone. The synthesis reaction starts by completion of the acid treatment in the activation treatment.

Three types of patterns are allowed as forms of the addition of a β-diketone to an iridium compound solution as described above, because the activation of an iridium compound is necessary for progress of the synthesis reaction of tris(β-diketonato)iridium, and the activation of an iridium compound is exerted after the completion of each of the alkali treatment and the acid treatment.

Meanwhile, when the above-described three types of addition timing of the β-diketone are considered, a "solution before alkali (acid) addition" that is the standard of pH adjustment in addition of alkali or acid in the activation treatment means a solution before addition of alkali (acid) exactly as stated. That is, when a β-diketone is added after completion of the activation treatment of an iridium compound, a "solution" before alkali addition is an iridium compound solution. On the other hand, when a β-diketone is added previously to an iridium compound solution before application of the activation treatment (alkali treatment), a "solution" before the alkali addition is a mixed solution of the iridium compound solution and the β-diketone. Further, when a β-diketone is added to an iridium compound solution in an intermediate process between the alkali treatment and the acid treatment, a "solution" before the alkali addition is the iridium compound solution alone, but a "solution" before the acid addition is a mixed solution of the iridium compound solution and the β-diketone.

In addition, when a β-diketone is added to an iridium compound solution, pH of the iridium compound solution may fluctuate (in many cases, pH does not fluctuate) depending on the kind of the β-diketone. When a mixed solution of an iridium compound solution and a β-diketone corresponds to the solution before the alkali (acid) addition, a value in a state of the mixed solution is adopted as pH of the solution. Meanwhile, the same is applicable to the calculation standard of suitable pH difference by the alkali (acid) addition described above.

Furthermore, as to conditions of reaction between an iridium compound and a β-diketone, the addition amount of the β-diketone may be more than an equivalent number of an iridium complex to be manufactured (three equivalents relative to iridium). The β-diketone is preferably added in not less than 3 equivalents and not more than 20 equivalents relative to iridium.

An iridium compound solution for which the activation treatment has completed and which contains a β-diketone may be heated for progressing more effectively the synthesis reaction of tris(β-diketonato)iridium. The activation treatment may be applied at room temperature, but the synthesis reaction of tris(β-diketonato)iridium can improve the yield by heating to room temperature or higher temperatures. Reaction temperature in this case is preferably kept at not less than 50° C. and not more than 100° C. Reaction time is preferably set to not less than 0.5 hours and not more than 24 hours.

In the reaction liquid after the complex synthesis reaction, a generated iridium complex is precipitated. It is possible to obtain tris(β-diketonato)iridium with high purity by purification, after subjecting the precipitate to solid-liquid separation and washing the solid content.

Advantageous Effects of Invention

As described above, the present inventive method for manufacturing tris(β-diketonato)iridium can coordinate a wide variety of β-diketones to iridium. Hereby, the possibility of manufacturing tris(β-diketonato)iridium having various characteristics is broadened, which can establish a foundation for developing compounds suitable for phosphorescent materials such as an organic electroluminescence element and a raw material for forming a thin film.

MODE FOR CARRYING OUT THE INVENTION

Hereinafter, suitable embodiments of the present invention will be described. As described above, in the present inventive method for manufacturing tris(β-diketonato) iridium, there are three patterns as timing of the addition of a β-diketone to a solution of an iridium compound, that is, (1) a method of adding a β-diketone to an iridium compound solution for which the activation treatment has completed, (2) a method of adding previously a β-diketone to an iridium compound solution prior to applying each of the alkali treatment and the acid treatment, and (3) a method of adding a β-diketone to an iridium compound solution in the middle of the activation treatment (in an intermediate stage between the alkali treatment and the acid treatment). In the present embodiments, iridium complexes were manufactured based on the (1) to (3) procedures.

First Embodiment

In the present embodiment, an iridium complex was manufactured according to the procedure (1). Here, iridium (III) nitrate (Ir(NO$_3$)$_3$) was used as an iridium compound being a starting material, with which 1,1,1,6,6,6-hexafluoro-2,4-pentanedione (another name: hexafluoroacetylacetone) was reacted as a β-diketone, and tris(1,1,1,6,6,6-hexafluoro-2,4-pentanedionato)iridium (tris(hexafluoroacetylacetonato) iridium) was manufactured.

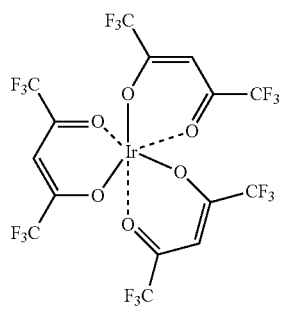

[Chem. 7]

There was prepared an iridium nitrate solution in which 18.8 mL of distilled water was added to 20.26 g of iridium nitrate having concentration of 9.1 wt % (iridium content: 1.84 g, 9.6 mmol)). The iridium nitrate solution was a navy aqueous solution and had pH 0.7.

For the iridium nitrate solution, the alkali treatment and the acid treatment were applied for the activation treatment. In the alkali treatment, a 1 N sodium hydroxide solution was added. In the alkali treatment, pH (0.7) of the iridium nitrate solution before the alkali addition was raised to an alkaline side. In the present embodiment, the alkali addition amount is adjusted so as to give a solution of a different pH value. After the alkali addition, the iridium nitrate solution was left at rest at room temperature for 1 hour.

Then, 6% diluted nitric acid was added to the solution as the acid treatment. In the acid treatment, too, the acid addition amount is adjusted so as to give a different pH value. Meanwhile, in the above-described alkali treatment and acid treatment, the solution did not show a large change in appearance and was a navy aqueous solution.

19.5 g, 59.2 mmol of 1,1,1,6,6,6-hexafluoro-2,4-pentanedione was added to the iridium nitrate solution for which the alkali treatment and the acid treatment were applied to complete the activation treatment. The addition amount corresponds to 6 equivalents relative to 1 mol of iridium. After the addition of 1,1,1,6,6,6-hexafluoro-2,4-pentanedione, the solution was heated to 55° C. and held for 2.5 hours for a reaction.

The reaction liquid after the reaction became a dark yellow suspension. pH of the reaction liquid was slightly lowered to an acidic side. The reaction liquid was filtrated and subjected to solid-liquid separation, and the solid content was washed and then was purified with a column (solvent; hexane:ethyl acetate=5:1) and tris(1,1,1,6,6,6-hexafluoro-2,4-pentanedionato)iridium was collected.

The synthesized and collected iridium complex was analyzed by 1H NMR (proton nuclear magnetic resonance) and X-ray structural analysis. Here, 1H NMR was confirmed by 1H NMR apparatus (400 MHz) analysis using CDCl$_3$ as a measurement solvent. In addition, a method of X-ray structural analysis used a single crystal X-ray structural analysis apparatus (VariMax with RAPID) for analysis. The X-ray structural analysis was used together with 1H NMR, because 1H NMR alone is insufficient for the analysis of tris(1,1,1,6,6,6-hexafluoro-2,4-pentanedionato)iridium in which 1,1,1,6,6,6-hexafluoro-2,4-pentanedione being a symmetric β-diketone is coordinated. Then, as the result of these analyses, it was confirmed that the iridium complex manufactured this time was surely tris(1,1,1,6,6,6-hexafluoro-2,4-pentanedionato)iridium. Together with the confirmation, yield was calculated for the collected iridium complex (calculated from iridium quantity).

The present embodiment tried a synthesis of an iridium complex based on a conventional method of not applying the alkali treatment and the acid treatment, in addition to a test example of applying the alkali treatment and the acid treatment. Further, a case was also investigated where the alkali treatment alone was applied without application of the acid treatment.

The present embodiment measures pH of the iridium compound solution at each step of the alkali treatment, the acid treatment, and the addition of a β-diketone. The pH measuring method performed measurement after immersing a pH composite electrode (directly reads the potential difference between a glass electrode and a comparative electrode each integrated with a temperature sensor) in three standard solutions of pH 6.86, pH 4.01 and pH 9.18, and carrying out three-point calibration.

In relation to results of synthesis tests of tris(1,1,1,6,6,6-hexafluoro-2,4-pentanedionato)iridium in the present embodiment, there are listed pH values after the alkali treatment, the acid treatment and the addition of the β-diketone, and yields in Table 1.

TABLE 1

| | Ir compound | | Alkali treatment | | Acid treatment | | β-diketone | | |
|---|---|---|---|---|---|---|---|---|---|
| | Kind | pH | Kind | pH | Kind | pH | Kind | pH | Yield |
| Example 1 | Ir(NO$_3$)$_3$ | 0.7 | NaOH | 10 | HNO$_3$ | 6 | hfp | 5 | 8% |
| Example 2 | | | | 11 | | 6 | | 5 | 10% |
| Example 3 | | | | 12 | | 6 | | 5 | 16% |
| Example 4 | | | | 13 | | 12 | | 11 | 29% |

TABLE 1-continued

|  | Ir compound | | Alkali treatment | | Acid treatment | | β-diketone | | |
|---|---|---|---|---|---|---|---|---|---|
|  | Kind | pH | Kind | pH | Kind | pH | Kind | pH | Yield |
| Example 5 |  |  |  | 13 |  | 10 |  | 9 | 30% |
| Example 6 |  |  |  | 13 |  | 8 |  | 7 | 29% |
| Example 7 |  |  |  | 13 |  | 6 |  | 5 | 25% |
| Example 8 |  |  |  | 13 |  | 3 |  | 3 | 14% |
| Comparative example 1 |  |  |  | 13 |  | 1 |  | 1 | 0% |
| Comparative example 2 |  |  |  | 9 |  | 6 |  | 5 | 0% |
| Comparative example 3 |  |  |  | 7 |  | 6 |  | 5 | 0% |
| Comparative example 4 |  |  | — | 0.7 | — | 0.7 |  | 0.7 | 0% |
| Comparative example 5 |  |  | NaOH | 5 | — |  | 5 | 3 | 0% | hfp: 1,1,1,6,6,6-hexafluoro-2,4-pentanedione

From Table 1, it is known that tris(1,1,1,6,6,6-hexafluoro-2,4-pentanedionato)iridium can be synthesized by the activation treatment in which the alkali treatment and the acid treatment are combined (Examples 1 to 8). In the activation treatment, it is known that appropriate pH in treatment exists in each of the alkali treatment and the acid treatment. That is, in the alkali treatment, it is required to set pH to not less than 10 while raising pH to an alkaline side by the alkali addition and, in addition, and, in Comparative Examples 2 and 3 that do not include the requirement, the synthesis of the iridium complex was not confirmed. Further, in the acid treatment, too, it is required not to simply shift the solution to an acidic side but to set the pH difference to not less than 0.1 and not more than 10, and, in Comparative Example 1 that does not include the requirement, the synthesis of the iridium complex was not confirmed. Further, the synthesis of the iridium complex was not confirmed in Comparative Example 4 that does not apply the alkali treatment and the acid treatment, and in Comparative Example 5 that applies the alkali treatment alone. Meanwhile, in these test examples in which the synthesis of the iridium complex was not confirmed, no change was observed in the solution, and, further, the targeted material was not observed when the solution was analyzed by thin-layer chromatography (TLC).

Second Embodiment

In the present embodiment, an iridium complex was manufactured according to the procedure of (2). As an iridium compound being a starting material, iridium (III) chloride (IrCl$_3$·nH$_2$O) was used, with which 1,1,1-trifluoro-2,4-hexanedione as a β-diketone was reacted to thereby manufacture tris(1,1,1-trifluoro-2,4-hexanedionato)iridium.

[Chem. 8]

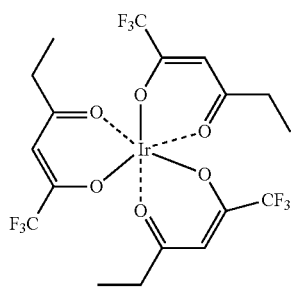

The present embodiment is a method of adding previously a β-diketone to an iridium compound solution and then applying the activation treatment. First, there was prepared an iridium chloride solution obtained by adding 94 mL of distilled water to 10.0 g of iridium chloride (iridium content of 5.2 g). Further, 25.9 g, 168.1 mmol of 1,1,1-trifluoro-2,4-hexanedione was added to the solution. The addition amount corresponds to 6 equivalents relative to 1 mol of iridium. No change in the appearance of the solution was observed when 1,1,1-trifluoro-2,4-hexanedione was added to the iridium chloride solution, and it was confirmed that no reaction was generated.

Then, the alkali treatment and the acid treatment were applied to the mixed solution. In the present embodiment, a 1 N sodium carbonate solution was used in the alkali treatment. In the acid treatment, 6% acetic acid was used. The method of the activation treatment is basically the same as in the first embodiment.

After application of the alkali treatment and the acid treatment, the mixed solution was heated to 55° C. and held for 2.5 hours for a reaction. The solution after the reaction became a dark yellow suspension. The reaction liquid was filtrated and subjected to solid-liquid separation, and the solid content was washed and then purified with a column, and tris(1,1,1-trifluoro-2,4-hexanedionato)iridium was collected. The synthesized iridium complex was analyzed by $^1$H NMR, and it was confirmed that the iridium complex was surely tris(1,1,1-trifluoro-2,4-hexanedionato)iridium. Further, the yield of the iridium complex was calculated.

In the present embodiment, too, a method of not applying the alkali treatment and the acid treatment was investigated, and a case of applying the acid treatment alone was investigated. In relation to results of synthesis tests of tris(1,1,1-trifluoro-2,4-hexanedionato)iridium in the present embodiment, there are listed pH values after the alkali treatment, the acid treatment and the addition of the β-diketone, together with yields in Table 2. Meanwhile, each of the pH measuring method and the method of $^1$H NMR at each step in the present embodiment was the same as in the first embodiment.

TABLE 2

| | Ir compound | | β-diketone | | Alkali treatment | | Acid treatment | | Yield |
|---|---|---|---|---|---|---|---|---|---|
| | Kind | pH | Kind | pH | Kind | pH | Kind | pH | |
| Example 9 | IrCl$_3$ | 2 | tfh | 2 | Na$_2$CO$_3$ | 10 | CH$_3$COOH | 6 | 3% |
| Example 10 | | | | 2 | | 11 | | 6 | 5% |
| Example 11 | | | | 2 | | 12 | | 6 | 8% |
| Example 12 | | | | 2 | | 13 | | 12 | 14% |
| Example 13 | | | | 2 | | 13 | | 10 | 16% |
| Example 14 | | | | 2 | | 13 | | 8 | 14% |
| Example 15 | | | | 2 | | 13 | | 5 | 12% |
| Example 16 | | | | 2 | | 13 | | 3 | 3% |
| Comparative example 6 | | | | 2 | | 13 | | 1 | 0% |
| Comparative example 7 | | | | 2 | | 9 | | 6 | 0% |
| Comparative example 8 | | | | 2 | | 7 | | 5 | 0% |
| Comparative example 9 | | | | 2 | — | 2 | — | 2 | 0% |
| Comparative example 10 | | | | 2 | — | 2 | CH$_3$COOH | 1 | 0% | tfh: 1,1,1-trifluoro-2,4-hexanedione

It can be confirmed that the iridium complex can be synthesized by the activation treatment even when β-diketones are added to an iridium compound solution before a reaction (Examples 9 to 16). Further, it is known that the necessity of the alkali treatment and the acid treatment and a suitable pH range and pH difference in each treatment have the same tendency as in the first embodiment. Meanwhile, in the present embodiment, a method of applying the acid treatment alone was also tried, but a complex was not synthesized (Comparative Example 10).

Third Embodiment

In the present embodiment, an iridium complex was manufactured according to the procedure of (3). Ammonium hexachloroiridate (III) ((NH$_4$)$_3$[IrCl$_6$]) was used as an iridium compound being a starting material, with which 1,1,1-trifluoro-2,4-pentanedione (1,1,1-trifluoroacetylacetone) was reacted as a β-diketone, to thereby manufacture tris(1,1,1-trifluoro-2,4-pentanedionato)iridium (tris(1,1,1-trifluoroacetylacetonato)iridium).

[Chem. 9]

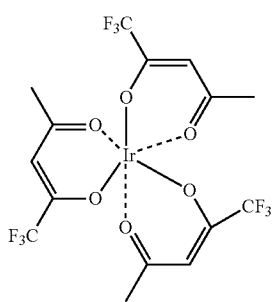

The embodiment, after applying the alkali treatment to an ammonium hexachloroiridate solution, adds 1,1,1-trifluoro-2,4-pentanedione thereto, and thereafter applies the acid treatment.

First, there was prepared an ammonium hexachloroiridate solution in which 470 mL of distilled water was added to 10.05 g of ammonium hexachloroiridate (iridium content of 4.06 g, 21.1 mmol). Then, the ammonium hexachloroiridate solution was subjected to the alkali treatment. The alkali treatment added a 1 N potassium hydroxide solution. After the alkali addition, the ammonium hexachloroiridate solution was left at rest for 1 hour.

25.9 g, 168.1 mmol of 1,1,1-trifluoro-2,4-pentanedione was added to the ammonium hexachloroiridate solution subjected to the alkali treatment. The addition amount corresponds to 6 equivalents relative to 1 mol of iridium.

Then, the acid treatment was applied to the solution. The acid treatment used 6% phosphoric acid. In the pH adjustment by the acid treatment, a mixed solution of the ammonium hexachloroiridate solution and 1,1,1-trifluoro-2,4-pentanedionato was used as a solution before the adjustment, and pH was adjusted to an acidic side value with reference to the pH of the solution before the adjustment. After the acid treatment, the solution was heated to 55° C. and held for 2.5 hours for a reaction.

The reaction liquid after the reaction became a dark yellow suspension. The reaction liquid was filtrated and subjected to solid-liquid separation, and the solid content was washed and then purified with a column (solvent; hexane: ethyl acetate=5:1) and tris(1,1,1-trifluoro-2,4-pentanedionato)iridium was collected. The synthesized iridium complex was analyzed by $^1$H NMR, and it was confirmed that the iridium complex was surely tris(1,1,1-trifluoro-2,4-pentanedionato)iridium. Further, the yield was calculated.

In the present embodiment, too, there were investigated a method of not applying the alkali treatment and the acid treatment, and a case of applying the acid treatment alone. In relation to results of synthesis tests of tris(1,1,1-trifluoro-2,4-pentanedionato)iridium in the present embodiment, there are listed pH values after the alkali treatment, the acid treatment and the addition of the β-diketone, together with yields in Table 3. Meanwhile, each of the pH measuring method and the method of $^1$H NMR at each step in the present embodiment was the same as in the first embodiment.

TABLE 3

| | Ir compound | | Alkali treatment | | β-diketone | | Acid treatment | | |
|---|---|---|---|---|---|---|---|---|---|
| | Kind | pH | Kind | pH | Kind | pH | Kind | pH | Yield |
| Example 17 | (NH₄)₃IrCl₆ | 5 | KOH | 10 | tfp | 9 | H₃PO₄ | 6 | 4% |
| Example 18 | | | | 11 | | 10 | | 6 | 7% |
| Example 19 | | | | 12 | | 11 | | 6 | 14% |
| Example 20 | | | | 13 | | 12 | | 11 | 23% |
| Example 21 | | | | 13 | | 12 | | 10 | 25% |
| Example 22 | | | | 13 | | 12 | | 8 | 24% |
| Example 23 | | | | 13 | | 12 | | 5 | 11% |
| Example 24 | | | | 13 | | 12 | | 3 | 4% |
| Comparative example 11 | | | | 13 | | 12 | | 1 | 0% |
| Comparative example 12 | | | | 9 | | 8 | | 6 | 0% |
| Comparative example 13 | | | | 7 | | 6 | | 5 | 0% |
| Comparative example 14 | | | — | 5 | | 5 | — | 5 | 0% |
| Comparative example 15 | | | — | 5 | | 5 | H₃PO₄ | 3 | 0% | tfp: 1,1,1-trifluoro-2,4-pentanedione

It can be confirmed that it is possible to synthesize the iridium complex by applying the acid treatment to accomplish the activation treatment, even when the β-diketone was added between the alkali treatment and the acid treatment, that is, in the middle of the activation treatment (Examples 17 to 24). In the method, too, It was confirmed that whether or not the complex could be synthesized was determined by the pH range or pH difference in the alkali treatment or the acid treatment.

INDUSTRIAL APPLICABILITY

As described above, the present invention allows a wide variety of β-diketones to be coordinated to iridium. The present inventive method is useful as a method for manufacturing raw material compounds for chemical deposition such as a CVD method and an ALD method, and, in addition, is also useful as a method for manufacturing raw materials (intermediate raw materials) of phosphorescent materials for organic light-emitting elements such as an organic EL element and organic ECL element. The present invention is useful as means for broadening the possibility of manufacturing tris(β-diketonato)iridium in various applications.

The invention claimed is:

1. A method for manufacturing tris(β-diketonato)iridium shown by Chem 2 in which a β-diketone is coordinated to iridium, by reacting the β-diketone shown by Chem 1 with an iridium compound which is any one of iridium nitrate (III, IV), iridium chloride (III, IV), and ammonium hexachloroiridate (III, IV), wherein
  an activation treatment including (a) an alkali treatment and (b) an acid treatment described below is applied to the iridium compound to activate the iridium compound, and to subsequently react the β-diketone,
  (a) an alkali treatment: a treatment of adding alkali to a solution of the iridium compound to raise pH of the solution to a more alkaline side than that before the alkali addition and to not less than 10, and
  (b) an acid treatment: a treatment of adding acid to the solution subjected to the alkali treatment to lower pH of the solution to a more acidic side than that before the acid addition and to make the pH difference between solutions before and after the acid addition be not less than 0.1 and not more than 10,

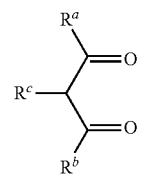

[Chem 1]

wherein each of Ra and Rb is a hydrocarbon group or substituents in which a hydrogen atom in a hydrocarbon group is substituted by a halogen atom, Ra and Rb may be different substituents, or identical substituents, Rc is a substituent composed of any of a hydrogen atom, a halogen atom and a hydrocarbon group; and

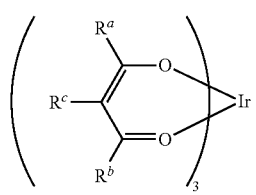

[Chem 2]

wherein Ra, Rb, and Rc have the same meaning as in Chem 1.

2. The method for manufacturing tris(β-diketonato)iridium according to claim 1, wherein pH after alkali addition in the alkali treatment (a) is set to not less than 12.

3. The method for manufacturing tris(β-diketonato)iridium according to claim 1, wherein the pH difference between solutions before and after the alkali addition in the alkali treatment (a) is set to not less than 2 and not more than 13.

4. The method for manufacturing tris(β-diketonato)iridium according to claim 1, wherein the pH difference between solutions before and after the acid addition in the acid treatment (b) is set to not less than 1 and not more than 10.

5. The method for manufacturing tris(β-diketonato) iridium according to claim 2, wherein the pH difference between solutions before and after the alkali addition in the alkali treatment (a) is set to not less than 2 and not more than 13.

6. The method for manufacturing tris(β-diketonato) iridium according to claim 2, wherein the pH difference between solutions before and after the acid addition in the acid treatment (b) is set to not less than 1 and not more than 10.

7. The method for manufacturing tris(β-diketonato) iridium according to claim 3, wherein the pH difference between solutions before and after the acid addition in the acid treatment (b) is set to not less than 1 and not more than 10.

* * * * *